United States Patent [19]

Angyan et al.

[11] 4,405,353

[45] Sep. 20, 1983

[54] CARBOFURAN-CONTAINING PLANT PROTECTING COMPOSITIONS

[75] Inventors: Sandor Angyan; Istvan Racz; Erzsebet Radvanyi; Ferenc Kovats; Tamas Detre; Jozsef Sos, all of Budapest, Hungary

[73] Assignee: Chinoin Gyogyszer es Vegyeszeti Termekek Gyara Rt., Budapest, Hungary

[21] Appl. No.: 211,321

[22] Filed: Nov. 26, 1980

[30] Foreign Application Priority Data

Nov. 28, 1979 [HU] Hungary .............................. CI 1991

[51] Int. Cl.$^3$ ...................... A01N 25/12; A01N 43/08
[52] U.S. Cl. ......................................... 11/3; 424/285;
424/362; 71/DIG. 1
[58] Field of Search ................... 424/285; 71/DIG. 1, 71/3

[56] References Cited

U.S. PATENT DOCUMENTS

| | | | |
|---|---|---|---|
| 2,974,030 | 3/1961 | Geary | 71/3 |
| 3,030,734 | 5/1962 | Brickey | 71/3 |
| 3,474,171 | 10/1969 | Scharpf | 424/285 |
| 3,547,955 | 12/1970 | Scharpf | 424/285 |
| 3,564,605 | 2/1971 | Scharpf | 424/285 |
| 3,649,241 | 3/1972 | Fitzgerald et al. | 71/DIG. 1 |
| 4,125,392 | 11/1978 | Primo | 71/DIG. 1 |

FOREIGN PATENT DOCUMENTS 2655398 6/1978 Fed. Rep. of Germany ............ 71/3
170617 7/1974 Hungary .

OTHER PUBLICATIONS

Pesticides Formulations edited by Wade van Valkenburg, pp. 146, 147.
Hungarian Article; K. Farkas, I. Racz–S. Angyan; pp. 395–402, (Article Submitted Concurrently with Applicant's *Curriculum Vitae*).
Journal of Economic Entomology., vol. 64, No. 1, pp. 172–175; C. D. Pless et al: "Growth and Yield of Burley Tobacco as Affected by Two Systemic Insecticides".

*Primary Examiner*—Glennon H. Hollrah
*Attorney, Agent, or Firm*—Karl F. Ross; Herbert Dubno

[57] ABSTRACT

The invention relates to carbofurane-containing plant protecting compositions. More particularly, the invention concerns insecticide compositions with improved plant growth accelerating properties, containing 1 to 50% by weight of 2,3-dihydro-2,3-dimethyl-7-benzofuranol methylcarbamate optionally along with usual amounts of additives conventionally used in the manufacture of plant protecting compositions, which comprises 50 to 99% by weight of a carrier granulate prepared by partial hydrolysis of vegetable waste matters, preferably corn-cob, corn-stalk, chopped wood or sawdust derived from broad leaved trees, rice hull, read or broaken reed, known per se.

6 Claims, No Drawings

CARBOFURAN-CONTAINING PLANT PROTECTING COMPOSITIONS

The invention relates to plant protecting compositions containing a usual amount of 2,3-dihydro-2,2-dimethyl-7-benzofuranol methylcarbamate (furtheron referred to as carbofuran) optionally along with usual amounts of additives conventionally used in the manufacture of plant protecting compositions.

The compositions according to the invention contain 50 to 99% by weight of a carrier prepared by a partial hydrolysis of vegetable waste matter, preferably corn cobs, corn stalks, chopped wood or sawdust derived from broad leaved trees, rice hulls, reeds or broaken reeds, and have improved plant growth accelerating properties. According to the invention the new compositions are prepared by coating and/or saturating the carrier with a solution or suspension of carbofuran, optionally adding further additives and finally drying the composition.

The Hungarian Patent No. 170,617 discloses carriers for plant protecting compositions. These carriers can be prepared by hydrolyzing agricultural waste matters and have favorable mechanical and sorption properties. While certain components of these carriers may be utilized by the plants, they are absolutely inert with respect to the active ingredient of the plant protecting composition.

It has been found that the insecticide carbofuran when applied for example to tabacco, or maize accelerates the growth and ripening of plants and increases the crop yield. This effect considerably exceeds what could have been expected simply as a consequence of the elimination or diminution of the damage done by insects [J. Econ. Entomol. 172, 64 (1971)].

The present invention is based on the surprising recognition that if the insecticidally active carbofuran is applied to a carrier disclosed in the Hungarian Patent No. 170,617 or prepared from other agricultural waste matters in an analogous way, the composition obtained shows a considerably higher plant growth accelerating activity than carbofuran alone.

The increase of plant growth accelerating activity is highly surprising since according to the Hungarian Patent referred to above the carriers employed "due to their composition and way of preparation can be considered as practically entirely inert with respect to biologically active compounds".

On the other hand, it could not be expected either that the components of these carriers, which may optionally be utilized by the plants, in a very small ("catalytic") amount, which is only a fraction of the amount required for traditional fertilization exert such a favorable effect on the function of the organism of plants.

It has been observed that as a result of a treatment with the compositions according to the invention the weight of the overground parts of plants in an early stage of their development had considerably been increased, a thickening of the stalk was manifest and the size of the leaves has also been increased.

It was also observed that the leaf-green level of the tomato test plants and maize, wheat, tobacco and sugar beets in field trials was increased, and accordingly the visual observation clearly showed that the leaves were definitely greener than the untreated ones. It has also unexpectedly been found that carbofuran exerted a greater effect on the root growth when the carriers disclosed in the present invention have been employed, and accordingly, the test plants had thicker, ramifying, and longer roots and more capillary roots have been developed.

To illustrate the effect of the compositions according to the invention the composition prepared according to Example 1 was tested. For comparison plants treated with (a) a solution of carbofuran,
(b) a known carbofuran-containing composition and
(c) untreated plants were used.

The biological tests were carried out as follows:

Pots having an area of 228 cm² were filled with loamy garden soil to a depth of 5 cm. The soil for different tests was obtained from different places. Tomato seeds of "Harrow" type were then placed on the surface of the soil.

The test materials and compositions, respectively were applied to the whole surface, directly to the plants.

(a) Granules were homogenized with 3 cm² washed river sand and were uniformly sprinkled on to the surface of the pots.
(b) When testing the active ingredient alone, the whole surface was treated with a saturated carbofuran solution containing 700 ppm of active ingredient by means of a dropping tube.

The seeds were then covered with 50 cm³ (228 cm², passed through a 1-3 mm screen) crumbly soil. The pots were kept in a greenhouse at 18°-25° C., and a humidity of 60 to 90%. After 28 and 35 days, respectively the weight of 25 plants was measured and the mathematical average was calculated.

6 repetitions were made. The results given correspond to the average of 6×25=150 measurements. the results are shown in the following Table.

TABLE

| Composition | Amount employed expressed in carbofurane [kg/ha] | | Weight of seedling on the 28th day after treatment | | Weight of seedling on the 35th day after treatment | |
| --- | --- | --- | --- | --- | --- | --- |
| | carrier parts | carbofurane parts | [g] | % difference related to the control | [g] | % difference related to the control |
| Composition according to Example 1 | 20 | 2 | 5.61 | 32 | 8.39 | 42 |
| FURADAN ® 10 G | 20 | 2 | 4.58 | 8 | 6.50 | 10 |
| A saturated aqueous solution of carbofurane | | 2 | 5.46 | 28 | 7.05 | 19 |
| Untreated control | — | | 4.24 | 0 | 5.90 | 0 |

The results clearly show that the weight of the seedlings treated with the compositions according to the invention considerably exceeds the weight of the plants treated with a carbofuran solution and of the untreated plants, moreover an expressed weight increase could be observed also in comparison with the commercial carbofuran-containing composition FMC-Niagara FURADAN®10 G. It can also be seen that the difference between the plant growth accelerating activity of the compositions according to the invention and of the latter composition, where quartz is used as a carrier is greater than the difference related to the carbofuran solution. Since the quartz carrier is obviously inert with respect to the carbofuran active ingredient, the increase of the plant growth accelerating activity of carbofuran in the compositions according to the invention due to the carrier employed, is the sum of two factors:

(a) the carrier compensates the loss in activity related to the active ingredient alone, due to formulation;
(b) the carrier increases the activity in comparison with the active ingredient alone.

The surplus effect of the compositions according to the invention is due to the fact that the proteins, saccharides, carboxylic acids, furfural, various meso- and micro-nitriments in combination with carbofuran favorable influence the function of the vegetable organism.

The carriers used in the compositions according to the invention are prepared from various vegetable waste matters, preferably corn cob, chopped wood or sawdust prepared from broad leaved trees, rice hulls and reeds following the procedure described in the Hungarian Patent No. 170,617. More particularly, the vegetable waste matters are hydrolyzed with steam at 150° to 200° C., whereupon they are granulated for example with high-speed tube granulating equipment.

In the cited Hungarian Patent the carrier obtained is characterized as a carrier "of hydrolyzed agricultural waste matter origin, which consists of 35 to 45% by weight of cellulose related to its dry substance content, saccharides and/or carboxylic acids, has a pH of between 1 and 7 measured in a 10% aqueous suspension and a grain size of 0.1 to 10 mm". It should be noted, however, that according to the current results the composition of the carrier, especially if sawdust from broad leaved trees is used as starting material, can also slightly be different.

The carbofuran content of the compositions according to the invention is between 1 to 50% by weight, preferably 5 to 10% by weight, i.e. is in the same range as the carbofuran content of the commercially available carbofuran-containing compositions.

The compositions can be prepared starting from an aqueous or organic solution or suspension of carbofuran. As orgainc solvents chloroform, or petroleum can for example be used. In adiditon to the active ingredient and the carrier the compositions can contain also further additives, such as adhesives, e.g. film-forming agents, etc.

Further details of the invention are illustrated in the following Examples. It is, however, not intended to limit our invention to the Examples.

EXAMPLE 1

1360 kg./hour of corn cobs are hydrolyzed with steam at 80° C., under a pressure of 12 at. The corn cobs have the following characteristics:
grain size: 2 to 20 mm;
water content: 20.8%;
volume weight: 199 g./lit.;
pentose content related to dry substance: 33%;
lignin content related to dry substance: 30%;
cellulose content related to dry substance: 36%;
ash content related to dry substance: 1%.

1432 kg./hour of a hydrolyzate are obtained, which has the following properties:
grain size: 0.02 to 2 mm.;
water content: 42%;
wet volume weight: 500 g./lit.; furfurol content related to dry substance: 16%; lignin content related to dry substance: 35% and cellulose content related to dry substance: 40%.

The hydrolyzate is then granulated in high-speed knife, tube granulating equipment. 612 kg. of a granulate having a grain size of 0.1 to 1 mm. are obtained.

Further characteristics of the granulate are as follows: sorption capacity: 26.8 g./100 g. (from a 1:1 mixture of xylene and gasoline oil)
BET area: 2.4 m$^2$/g.
pH (in a 10% aqueous suspension): 5.7

The carrier granules obtained are then filled into a cylinder having a diameter of 200 mm. and height of 400 mm. and a capacity of 9 kg. The bottom of the cylinder is a perforated plate to the top of which a bag dust filter is attached and air is passed through it upwards from below. The carrier is brought in motion with an air stream of 1.5 m./sec. 1 kg. of carbofuran are dissolved in 6.8 kg. of chloroform and the solution is sprayed on the moving granulate. Air is through the system until chloroform is entirely evaporated. Carbofuran forms a uniform coating on the surface of the carrier. The composition obtained contains 10% by weight of carbofuran.

EXAMPLE 2

1200 kg. of waste wood are hydrolyzed with steam at 180° C., under 12 at. The basic material has the following characteristics:
grain size: 20 to 50 mm.;
water content: 18%;
volume weight: 180 g./lit.;
pentose content related to dry substance: 22%;
lignin content related to dry substance: 26%;
cellulose content related to dry substance: 42%;
ash content related to dry substance: 0.8%.

1470 kg./hour of a hydrolyzate are obtained, which has the following properties: grain size: 0.02 to 2 mm.;
water content: 52%;
wet volume weight: 500 g./lit.;
furfurol resin content related to dry substance: 10%;
lignin content related to dry substance: 30%;
cellulose content related to dry substance: 45%;
ash content related to dry substance: 1.2%.

The hydrolyzate obtained is then granulated in high-speed knife, tube granulating equipment. 620 kg. of a granulate having a grain size of 0.1 to 10 mm. are obtained.

Further characteristics of the granulate are as follows: sorption capacity: 78 g./100 g. (from a 1:1 mixture of xylene and gasoline oil)
BET area: 2.3 m$^2$./g.
pH: 3.6.

Then following the procedure described in Example 1 a composition containing 10% by weight of carbofuran are obtained.

EXAMPLE 3

2 kg. of crystalline carbofuran are suspended in 3.0 kg. of a hydrocarbon derivative having a low boiling point (petroleum) and the suspension is treated in a wet-grinding apparatus until a stable suspension is obtained. The grain size of carbofuran in the paste obtained preferably is about 1 to 10 μm. Into a 100-lit. concrete mixer 18 kg. of a carrier granulate prepared according to Example 1 are weighed. 5 kg. of the paste containing 40% by weight of carbofuran are sprayed on the mixed carrier and petroleum is evaporated by injecting hot air. A composition containing 10% by weight of carbofuran is obtained.

EXAMPLE 4

2 kg. of crystalline carbofuran are suspended in 3 kg. of water. The procedure described in Example 3 is then followed. A composition containing 10% by weight of carbofuran is obtained.

We claim:

1. An insecticidal composition with improved plant growth accelerating properties containing 1 to 50% by weight of 2,3-dihydro-2,2-dimethyl-7-benzofuranol methyl carbamate and 50 to 99% by weight of a carrier prepared by partial hydrolysis of granulated vegetable waste matter selected from the group consisting of corncobs, cornstalks, chopped wood or sawdust from broad-leafed trees, rice hulls, and reeds.

2. The insecticidal composition defined in claim 1 which consists essentially of 5 to 10% by weight carbofuran and the balance partially hydrolyzed granules of corncob as a carrier.

3. The insecticidal composition defined in claim 1 wherein the carrier is prepared by hydrolysis of the granulated vegetable waste matter by steam.

4. The insecticidal composition defined in claim 1 wherein the carrier comprises granules of vegetable waste matter having a particle size from 0.02 to 2 mm.

5. The insecticidal composition defined in claim 1 which consists essentially of 10% by weight carbofuran and the balance partially hydrolyzed granules of corncob.

6. A method of promoting plant growth which comprises the step of applying to a plant growth site an effective amount of a composition containing 1 to 50% by weight of carbofuran uniformly distributed on a steam hydrolyzed granulated vegetable waste carrier selected from the group consisting of corncobs, cornstalks, chopped wood or sawdust from broad leaved trees, rice hulls and reeds, said granulated vegetable waste carrier constituting the balance of the composition.

* * * * *